US007279442B2

United States Patent
Teshigahara et al.

(10) Patent No.: US 7,279,442 B2
(45) Date of Patent: Oct. 9, 2007

(54) PROCESS FOR PRODUCING CATALYST FOR PRODUCTION OF UNSATURATED ALDEHYDE AND UNSATURATED CARBOXYLIC ACID

(75) Inventors: Isao Teshigahara, Mie (JP); Nariyasu Kanuka, Mie (JP); Kazuharu Tazawa, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 172 days.

(21) Appl. No.: 11/033,131

(22) Filed: Jan. 12, 2005

(65) Prior Publication Data

US 2005/0165253 A1   Jul. 28, 2005

Related U.S. Application Data

(63) Continuation of application No. PCT/JP04/13459, filed on Sep. 15, 2004.

(30) Foreign Application Priority Data

Dec. 4, 2003  (JP) ............................. 2003-405586

(51) Int. Cl.
*B01J 23/00* (2006.01)
*C07C 51/16* (2006.01)
(52) U.S. Cl. .................. 502/311; 562/545; 562/547
(58) Field of Classification Search .................. None
See application file for complete search history.

(56) References Cited

U.S. PATENT DOCUMENTS 6,383,976 B1   5/2002   Arnold et al.

2003/0191344 A1*  10/2003  Yunoki ........................ 562/546

FOREIGN PATENT DOCUMENTS

| JP | 58-98143 | 6/1983 |
|---|---|---|
| JP | 3-109946 | 5/1991 |
| JP | 6-321536 | 11/1994 |
| JP | 2000-169149 | 6/2000 |
| JP | 2000-237592 | 9/2000 |
| JP | 3251641 | 11/2001 |
| JP | 3278246 | 2/2002 |
| JP | 2003-251183 | 9/2003 |

OTHER PUBLICATIONS

U.S. Appl. No. 11/032,072, filed Jan. 11, 2005, Teshigahara et al.
U.S. Appl. No. 11/032,050, filed Jan. 11, 2005, Teshigahara et al.
U.S. Appl. No. 11/033,271, filed Jan. 12, 2005, Teshigahara et al.
U.S. Appl. No. 11/044,187, filed Jan. 28, 2005, Teshigahara et al.
U.S. Appl. No. 11/045,123, filed Jan. 31, 2005, Tazawa et al.
U.S. Appl. No. 11/045,307, filed Jan. 31, 2005, Tazawa et al.
R2: Introduction of Catalysts Engineering, the last paragraph on p. 73, 72-74.

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process for producing a catalyst which has a high mechanical strength and is capable of producing an unsaturated aldehyde and an unsaturated carboxylic acid constantly over a long period of time and in good yield; and, a method for producing an unsaturated aldehyde or carboxylic acid from catalytic oxidation of an olefin, a tertiary butyl alcohol, or a methyl tertiary butyl ether substrate with a gas that contains molecular oxygen and the produced catalyst.

5 Claims, No Drawings

PROCESS FOR PRODUCING CATALYST FOR PRODUCTION OF UNSATURATED ALDEHYDE AND UNSATURATED CARBOXYLIC ACID

TECHNICAL FIELD

The present invention relates to a process for producing a catalyst which is a catalyst for gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid, and which has a high mechanical strength and is capable of producing the corresponding unsaturated aldehyde and unsaturated carboxylic acid constantly over a long period of time and in good yield.

BACKGROUND ART

Heretofore, various proposals have been made with respect to catalysts for gas phase catalytic oxidation of propylene with a molecular oxygen-containing gas to produce acrolein and acrylic acid, and catalysts for gas phase catalytic oxidation of isobutylene, tertiary butyl alcohol or methyl tertiary butyl ether with a molecular oxygen-containing gas to produce methacrolein and methacrylic acid.

These catalysts are, of course, required to be able to produce the desired corresponding unsaturated aldehyde and unsaturated carboxylic acid in good yield, but also required to have sufficiently high mechanical strength and durability durable for industrial use for a long period of time.

Heretofore, in order to improve the properties of the catalyst to be used for such a reaction, it has been proposed to control pores of the catalyst by using various organic compounds. As such examples, Patent Documents 1, 2 and 3, etc. are known. Such a method has a merit in that the pore size of a catalyst can relatively freely be changed by adding an organic compound having the type or grain size changed at the time of the production of the catalyst and removing the organic compound used by heat treatment. However, such a method has a problem that at the time of removal of the organic compound, sintering of the catalyst by combustion of the organic compound, or reduction of the catalyst by the organic compound takes place, whereby the activating treatment tends to be complicated, and reproducibility of the catalyst performance tends to be poor.

Further, Patent Document 4 proposes to use activated carbon at the time of producing a catalyst in order to improve the performance and mechanical strength of the catalyst. Namely, it is proposed that a mixture of the above-mentioned catalyst components is calcined, and activated carbon having a prescribed particle size is mixed to the obtained calcined product, followed by molding and heat treatment. However, also in this case, there is still a room for improvement with respect to the yield of the desired unsaturated aldehyde and unsaturated carboxylic acid.

Thus, a new process for producing a catalyst, whereby the catalyst performance can easily be improved or increased and is excellent in reproducibility, is desired.

Patent Document 1: JP-A-58-98143
Patent Document 2: JP-A-3-109946
Patent Document 3: JP-3278246
Patent Document 4: JP-3251641

DISCLOSURE OF THE INVENTION

Problem to be Solved by the Invention

In view of the above-described prior art, it is an object of the present invention to provide a process for producing a catalyst which is capable of gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid in good yield and with good reproducibility and which has a high mechanical strength and high durability.

Means to Solve the Problem

The present inventors have conducted an extensive research to solve the above problem and have found that in the production of a composite oxide catalyst containing at least molybdenum, bismuth and iron, to produce an unsaturated aldehyde and unsaturated carboxylic acid, the amount of moisture contained in the dried product obtained by drying a mixed solution or slurry containing catalyst components, followed by molding, is largely influential over the characteristics such as the activity, mechanical strength, etc. of the catalyst, and it is possible to solve the above problem by controlling it within a proper range.

Namely, by the study made by the present inventors, it has been found that a molded catalyst whereby the desired unsaturated aldehyde and unsaturated carboxylic acid can be produced in good yield with good reproducibility, and the mechanical strength is high and constant, can be obtained by molding while controlling the amount of moisture contained in a dried product obtained from a mixed solution or slurry containing the catalyst components, to a level of from 0.3 to 4 wt %, as will be seen in Examples and Comparative Examples given hereinafter. If the moisture content in the above dried product is smaller than 0.3 wt %, the molding pressure required to obtain good characteristics tends to be high, and it tends to be difficult to obtain a molded product of the catalyst having constant characteristics. On the other hand, in the case of a dried product having a moisture content of larger than 4 wt %, the characteristics of the catalyst tend to change in the calcining step following the molding, whereby it tends to be difficult to obtain a molded product of the catalyst having constant characteristics.

Thus, the present invention is characterized by the following constructions.

(1) A process for producing a catalyst for the production of an unsaturated aldehyde and an unsaturated carboxylic acid, which is a process for producing a composite oxide catalyst containing at least molybdenum, bismuth and iron, to be used at the time of gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid, characterized in that a mixed solution or an aqueous slurry, which contains the above catalyst components, is dried, the moisture content of the obtained dried product is adjusted to from 0.3 to 4 wt %, followed by tabletting to obtain a molded product.

(2) The process for producing a catalyst for the production of an unsaturated aldehyde and an unsaturated carboxylic acid according to the above (1), wherein the molded product is of a ring shape opened in the longitudinal direction and having an outer diameter of from 3 to 10 mm, an inner diameter being from 0.1 to 0.7 time the outer diameter and a length being from 0.5 to 2 times the outer diameter.

(3) The process for producing a catalyst for the production of an unsaturated aldehyde and an unsaturated carboxylic acid according to the above (1) or (2), wherein the composite oxide catalyst has the following formula (1):

   (1)

(wherein X is at least one element selected from the group consisting of Na, K, Rb, Cs and Tl, Y is at least one element selected from the group consisting of B, P, As and W, Z is at least one element selected from the group consisting of Mg, Ca, Zn, Ce and Sm, Q is a halogen, and a to k represent atomic ratios of the respective elements, and when a=12, b=0.5 to 7, c=0 to 10, d=0 to 10, c+d=1 to 10, e=0.05 to 3, f=0.0005 to 3, g=0 to 3, h=0 to 1, i=0 to 0.5 and j=0 to 40, and k is a numerical value which satisfies the oxidized states of other elements.)

(4) A method which comprises gas phase catalytic oxidation of an olefin, tertiary butyl alcohol or methyl tertiary butyl ether with a molecular oxygen-containing gas by using a catalyst obtained by the process as defined in any one of the above (1) to (3), to produce the respectively corresponding unsaturated aldehyde and unsaturated carboxylic acid.

(5) The method according to the above (4), wherein the olefin is propylene, and the unsaturated aldehyde and unsaturated carboxylic acid are acrolein and acrylic acid, respectively.

Effects of the Invention

According to the process of the present invention, it is possible to provide a catalyst which has a high mechanical strength and which is capable of gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid, constantly over a long period of time and in good yield, by a means based on a new concept such that at the time of producing a composite oxide catalyst containing at least molybdenum, bismuth and iron, tabletting is carried out while controlling the amount of moisture contained in the dried product obtained by drying a mixed solution or slurry containing the catalyst components, followed by molding, within a specific range.

BEST MODE FOR CARRYING OUT THE INVENTION

The catalyst to be produced by the present invention, is a catalyst for gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid and is a composite oxide catalyst containing at least molybdenum, bismuth and iron. The present invention is applicable to any catalyst so long as it is a composite oxide catalyst containing such three components. However, it is particularly preferably applicable to a catalyst represented by the following formula (1):

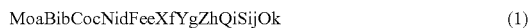   (1)

In the formula (1), Mo represents molybdenum, Bi bismuth, Co cobalt, Ni nickel, Fe iron, Si silicon and O oxygen, and X, Y, Z, Q, a to j and k are as defined above. Especially, the catalyst to be produced by the present invention is preferably one having the above formula (1) wherein Q is a chlorine atom, and it is particularly preferred that when a=12, b=0.5 to 7, c=0 to 10, d=0 to 10, c+d=1 to 10, e=0.05 to 3, f=0.0005 to 3, g=0 to 3, h=0 to 1, i=0 to 0.05 and j=0 to 40.

In the process of the present invention, raw material compounds containing the respective element components of the catalyst are suitably dissolved or dispersed in an aqueous medium, in amounts required depending upon the composition of the catalyst to be produced, to obtain a mixed solution or aqueous slurry containing the catalyst components. The raw materials for the respective catalyst components may, for example, be nitrates, ammonium salts, hydroxides, oxides, sulfates, carbonates, halides or acetates of the respective elements. For example, for molybdenum, ammonium paramolybdate, molybdenum trioxide or molybdenum chloride may, for example, be used. To the aqueous medium, a non-aqueous solvent such as an alcohol may be added in order to adjust the viscosity, as the case requires.

The mixed solution or aqueous slurry containing the catalyst components, is preferably thoroughly stirred and mixed in order to prevent localization of each component. Then, the mixed solution or aqueous slurry containing the catalyst components is dried. The drying may be carried out by various methods. For example, a spray dryer, slurry dryer or drum dryer may, for example, be used to obtain a powdery dried product. However, drying by means of a spray dryer is particularly preferred.

In the present invention, it is important to control the moisture content of the dried product preferably in a powder form, which is to be subjected to molding and which contains the catalyst components. As mentioned above, the moisture content of the dried product is adjusted to be from 0.3 to 4 wt %. The moisture content of the dried product is defined by the formula (2).

In the formula (2), W1 is the weight when the dried product is subjected to evaporation to dryness at 150° C. for 10 hours, and W2 is the weight of the dried product.

$$\text{Moisture content} = (W2-W1)/W1 \times 100 \qquad (2)$$

In the present invention, as the method to adjust the moisture content of the dried product to be subjected to molding, to be within the above range, the conditions for drying the mixed solution or aqueous slurry containing the catalyst components may be controlled, or proper humidification may be applied by a method of e.g. spraying moisture to the dried product once produced. In any case, the moisture content of the dried product is required to be adjusted to be within the above range. Especially, in the present invention, the moisture content of the dried product is preferably from 0.4 to 3 wt %.

As the molding method of the dried product, a tabletting method is employed from the viewpoint of the efficiency in molding and the nature of the molded product. The shape of the product may be any shape such as a spherical, cylindrical or ring-shape. Further, with respect to the size, various sizes may suitably be selected. However, it is particularly preferred that the molded product is of a ring-shape opened in a longitudinal (height) direction and having an outer diameter of from 3 to 10 mm, an inner diameter being from 0.1 to 0.7 time the outer diameter and a length (height) being from 0.5 to 2 times the outer diameter.

At the time of the above molding, in order to improve the mechanical strength or degradation of the molded product, commonly known inorganic fibers such as glass fibers, various whiskers, etc. may be used. Further, in order to control the physical properties of the catalyst to have good reproducibility, an additive which is commonly known as a binder, such as ammonium nitrate, cellulose, starch, polyvinyl alcohol or stearic acid, may also be used.

In the present invention, the molded product of the dried product containing the catalyst components thus obtained, is then calcined. The calcining is preferably carried out in the presence of an oxygen-containing gas preferably at from 400 to 650° C., particularly preferably at from 450 to 600° C., preferably for from 1 to 15 hours, particularly preferably for from 3 to 12 hours. For such calcining, an atmospheric calcining furnace may be employed. As such an atmospheric calcining furnace, there may, for example, be employed a method wherein the catalyst is packed in a fixed bed reactor and heating is carried out from the exterior while circulating an atmospheric gas, a method wherein the above fixed bed reactor is of a heat exchange type, a method wherein an atmospheric gas is circulated in the interior of a muffle furnace, a method wherein an atmospheric gas is circulated into the interior of a tunnel furnace, or a method wherein an atmospheric gas is circulated in the interior of a kiln furnace. Taking the efficiency for control of the atmospheric gas flow rate in the calcining into consideration, it is preferred to employ a method wherein the catalyst is packed in a fixed bed reactor and heating is carried out from the exterior while circulating an atmospheric gas, more preferably a method wherein the catalyst is packed into a heat exchange type fixed bed reactor, and heating is carried out from the exterior while circulating an atmospheric gas. As the atmospheric gas, not only air, but a mixed gas of inert gasses, such as air and nitrogen, may be employed. From the economical advantage, it is preferred to employ air.

A method for gas phase catalytic oxidation of an olefin, tertiary butyl alcohol or methyl tertiary butyl ether with a molecular oxygen-containing gas by means of the catalyst produced by the present invention to produce the respectively corresponding unsaturated aldehyde and unsaturated carboxylic acid, may be carried out by a conventional method. For example, as the reactor, a fixed bed tubular reactor may be employed. In such a case, the reaction may be a single flow process through the reactor, or may be a recycle process, and it may be carried out under such conditions as commonly employed in a reaction of this type.

For example, a mixed gas comprising from 1 to 15 vol % of propylene, from 3 to 30 vol % of molecular oxygen, from 0 to 60 vol % of steam, from 20 to 80 vol % of an inert gas such as nitrogen, carbon dioxide gas or the like, is introduced to a catalyst layer having the catalyst packed in each reactor having an internal diameter of preferably from 15 to 50 mm under a pressure of from 0.1 to 1 MPa at a space velocity (SV) of from 300 to 5000 hr$^{-1}$. Otherwise, in the present invention, in order to increase the productivity, the operation may be made under a higher load reaction condition, such as a higher raw material concentration or a higher space velocity.

EXAMPLES

Now, the present invention will be described in further detail with reference to Examples of the present invention. However, it should be understood that the present invention is by no means restricted to such Examples. In the following, the conversion, the selectivity and the yield are calculated by the following formulae. Further, the drop impact strength of the catalyst is one obtained as described below.

Conversion (mol %): (mols of reacted propylene/mols of supplied propylene)×100

Selectivity (mol %): ((mols of formed acrolein+mols of formed acrylic acid)/mols of reacted propylene)×100

Yield (mol %): ((mols of formed acrolein+mols of formed acrylic acid)/mols of supplied propylene)×100

Drop impact strength: In a stainless steel pipe having an inner diameter of 25 mm and a length of 1 m, which was vertically set, 20 g of a catalyst was dropped from the top and received on a stainless steel plate having a thickness of 2 mm, whereupon the weight of the catalyst remaining on the plate was measured, followed by sieving with a sieve of 10 mesh. The drop impact strength was obtained by the following formula.

Drop impact strength (%)=(weight of the catalyst remaining on the sieve/weight of the catalyst dropped)×100

Example 1

155.6 g of ammonium paramolybdate was dissolved in 500 ml of heated pure water. Then, 29.7 g of ferric nitrate, 85.5 g of cobalt nitrate and 42.7 g of nickel nitrate were dissolved in 150 ml of heated pure water. These solutions were gradually mixed with sufficient stirring to obtain a slurry. Then, 1.4 g of borax and 0.74 g of potassium nitrate were dissolved in 40 ml of pure water under heating and added to the above slurry. Then, 66.2 g of silica was added and thoroughly stirred. Then, 3.0 ml of nitric acid was added to 20 ml of pure water and 35.6 g of bismuth nitrate was further added and mixed with stirring.

This slurry was heated and dried and then subjected to thermal treatment in an air atmosphere at 300° C. for one hour. To the obtained granular solid, pure water was added, followed by wet pulverization. The obtained slurry was dried by a spray dryer under such conditions that the inlet temperature was 300° C., and the outlet temperature was 125° C. The moisture content of the obtained dried product was measured and found to be 1.5 wt %.

To the above dried product, 1.5 wt % of graphite was added and then molded by a tabletting machine into tablets having an outer diameter of 6 mm, an inner diameter of 3 mm and a height of 4 mm.

Then, the tabletted product was put into a calcining container, and calcining was carried out at 510° C. for 4 hours while circulating a small amount of air, to obtain a composite oxide catalyst. The catalyst calculated from the raw materials charged, is a composite oxide having the following atomic ratio.

Mo:Bi:Co:Ni:Fe:Na:B:K:Si=12:1:4:2:1:0.1:0.2:0.1:15

The drop impact strength of this catalyst was measured and found to be 98.5%.

30 ml of this catalyst was packed into a stainless steel reactor equipped with a niter jacket and having an inner diameter of 20 mm, and a mixed gas comprising 8 vol % of propylene, 67 vol % of air and 25 vol % of steam, was introduced at SV1800 (hr$^{-1}$) to carry out an oxidation reaction of propylene at a reaction bath temperature of 310° C. under atmospheric pressure, whereby the conversion of propylene was 98.3%, the selectivity was 95.2% and the yield was 93.7%.

Comparative Example 1

A catalyst was prepared in the same manner as in Example 1 except that the outlet temperature of the spray dryer was changed to 160° C. The moisture content of the dried product was 0.2 wt %. The drop impact strength of this catalyst was measured and found to be 90.1%.

An oxidation reaction of propylene was carried out in the same manner as in Example 1, whereby the conversion of propylene was 97.9%, the selectivity was 95.0%, and the yield was 93.0%.

Comparative Example 2

A catalyst was prepared in the same manner as in Example 1 except that the outlet temperature of the spray dryer was changed to 95° C. The moisture content of the dried product was 5.0 wt %.

The drop impact strength of this catalyst was measured and found to be 91.5%.

An oxidation reaction of propylene was carried out in the same manner as in Example 1, whereby the conversion of propylene was 97.8%, the selectivity was 94.8%, and the yield was 92.7%.

INDUSTRIAL APPLICABILITY

The catalyst produced by the process of the present invention, is used for gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid. The produced unsaturated and unsaturated carboxylic acid are useful in a wide range of applications as e.g. starting materials for various chemical products, monomers for common resins, monomers for functional resins such as water absorptive resins, flocculating agents or thickeners.

The entire disclosure of Japanese Patent Application No. 2003-405586 filed on Dec. 4, 2003 including specification, claims and summary is incorporated herein by reference in its entirety.

What is claimed is:

1. A process for producing a catalyst for the production of an unsaturated aldehyde and an unsaturated carboxylic acid, which is a process for producing a composite oxide catalyst containing at least molybdenum, bismuth and iron, to be used at the time of gas phase catalytic oxidation of an olefin, tertiary butyl alcohol or methyl tertiary butyl ether with a molecular oxygen-containing gas to produce the respectively corresponding unsaturated aldehyde and unsaturated carboxylic acid, characterized in that a mixed solution or an aqueous slurry, which contains the above catalyst components, is dried, the moisture content of the obtained dried product is adjusted to from 0.3 to 4 wt %, followed by tabletting to obtain a molded product.

2. The process for producing a catalyst for the production of an unsaturated aldehyde and an unsaturated carboxylic acid according to claim 1, wherein the molded product is of a ring shape opened in the longitudinal direction and having an outer diameter of from 3 to 10 mm, an inner diameter being from 0.1 to 0.7 time the outer diameter and a length being from 0.5 to 2 times the outer diameter.

3. The process for producing a catalyst for the production of an unsaturated aldehyde and an unsaturated carboxylic acid according to claim 1, wherein the composite oxide catalyst has the following formula (1):

$$Mo_aBi_bCo_cNi_dFe_eX_fY_gZ_hQ_iSi_jO_k \qquad (1)$$

(wherein X is at least one element selected from the group consisting of Na, K, Rb, Cs and Tl, Y is at least one element selected from the group consisting of B, P, As and W, Z is at least one element selected from the group consisting of Mg, Ca, Zn, Ce and Sm, Q is a halogen, and a to k represent atomic ratios of the respective elements, and when a=12, b=0.5 to 7, c=0 to 10, d=0 to 10, c+d=1 to 10, e=0.05 to 3, f=0.0005 to 3, g=0 to 3, h=0 to 1, i=0 to 0.5 and j=0 to 40, and k is a numerical value which satisfies the oxidized states of other elements).

4. A method which comprises gas phase catalytic oxidation of an olefin, tertiary butyl alcohol or methyl tertiary butyl ether with a molecular oxygen-containing gas by using a catalyst obtained by the process as defined in claim 1, to produce the respectively corresponding unsaturated aldehyde and unsaturated carboxylic acid.

5. The method according to claim 4, wherein the olefin is propylene, and the unsaturated aldehyde and unsaturated carboxylic acid are acrolein and acrylic acid, respectively.

* * * * *